(12) United States Patent
Campbell et al.

(10) Patent No.: US 6,471,664 B1
(45) Date of Patent: Oct. 29, 2002

(54) KNEE JOINT AND METHOD

(75) Inventors: James H. Campbell, Clarkston, MI (US); Derek M. Helenberger, Berkley, MI (US); Nicholas C. Zalinski, Madison Heights, MI (US)

(73) Assignee: Becker Orthopedic Appliance Company, Troy, MI (US)

( * ) Notice: Subject to any disclaimer, the term of this patent is extended or adjusted under 35 U.S.C. 154(b) by 0 days.

(21) Appl. No.: 09/525,646

(22) Filed: Mar. 15, 2000

(51) Int. Cl.[7] .................................................. A61F 5/00
(52) U.S. Cl. ........................................... 602/16; 602/26
(58) Field of Search ................................. 128/869, 882; 602/5, 16, 20, 23, 26

(56) References Cited

U.S. PATENT DOCUMENTS

| | | |
|---|---|---|
| 3,723,997 A | 4/1973 | Kolman |
| 3,833,942 A | 9/1974 | Collins |
| 4,214,577 A | 7/1980 | Hoy |
| 4,215,441 A | 8/1980 | Wilson |
| 4,433,679 A * | 2/1984 | Mauldin .................. 128/80 F |
| 4,489,717 A | 12/1984 | Moissonnier |
| 4,502,472 A | 3/1985 | Pansiera |
| 4,606,542 A | 8/1986 | Segal |
| 4,614,518 A | 9/1986 | Lehneis et al. |
| 4,842,608 A | 6/1989 | Marx et al. |
| 4,911,709 A | 3/1990 | Marlow et al. |
| 4,928,676 A | 5/1990 | Pansiera |
| 5,000,169 A | 3/1991 | Swicegood et al. |
| 5,052,379 A * | 10/1991 | Airy ......................... 128/80 C |
| 5,062,857 A | 11/1991 | Berringer et al. |
| 5,171,325 A | 12/1992 | Aulie |
| 5,201,776 A | 4/1993 | Freeman |
| 5,242,378 A * | 9/1993 | Baker .......................... 602/26 |
| 5,645,590 A | 7/1997 | van de Veen |
| 5,704,946 A | 1/1998 | Greene |
| 5,749,840 A * | 5/1998 | Mitchell ...................... 602/23 |
| 5,888,236 A | 3/1999 | van de Veen |
| 5,904,721 A | 5/1999 | Henry et al. |
| 6,010,474 A * | 1/2000 | Wycoki ........................ 602/26 |

* cited by examiner

Primary Examiner—Michael A. Brown
(74) Attorney, Agent, or Firm—Ryndak & Suri

(57) ABSTRACT

There is provided a mechanical orthotic device and method. The orthotic device and method utilize a torsion spring to provide resistance to restrain pivotal movement of upper and lower members between an extension and a flexion position.

34 Claims, 8 Drawing Sheets

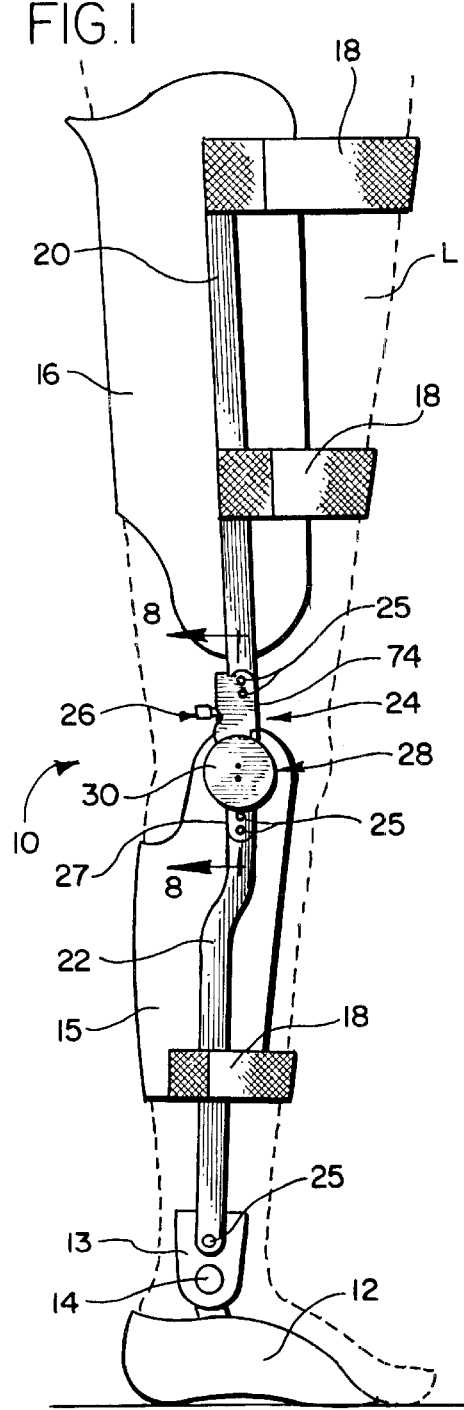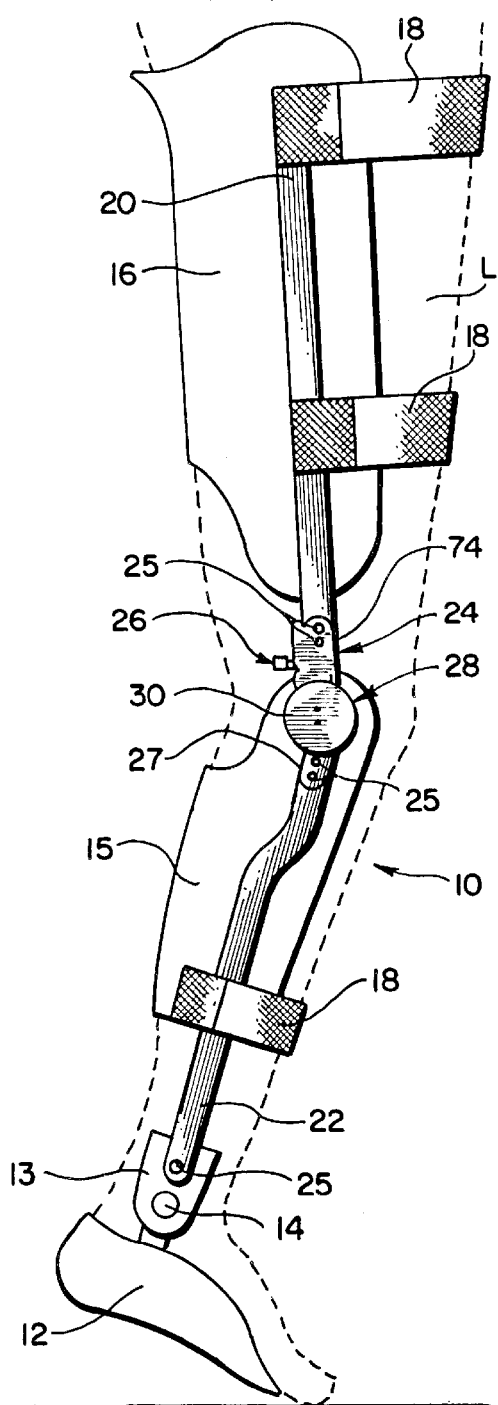

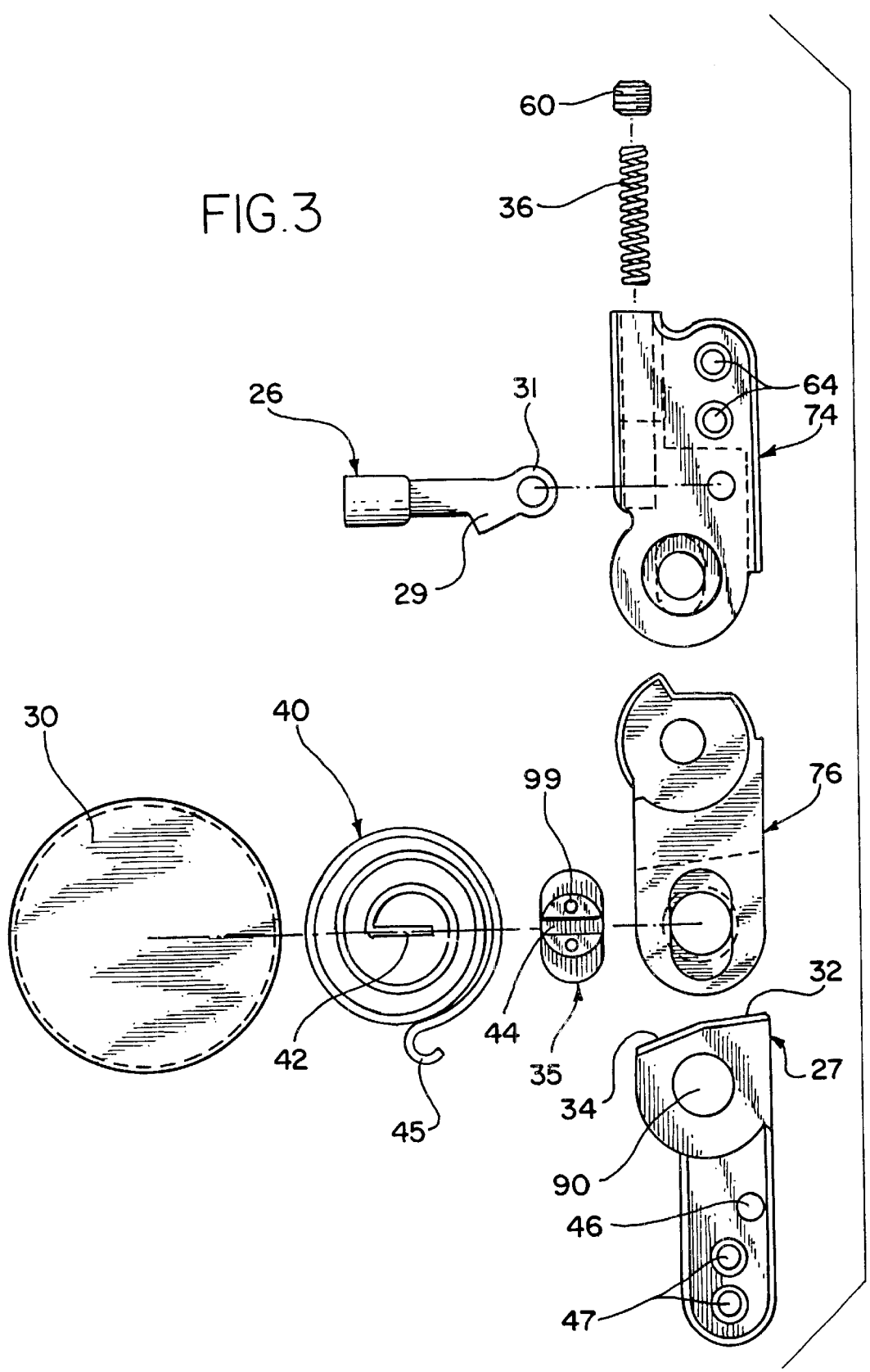

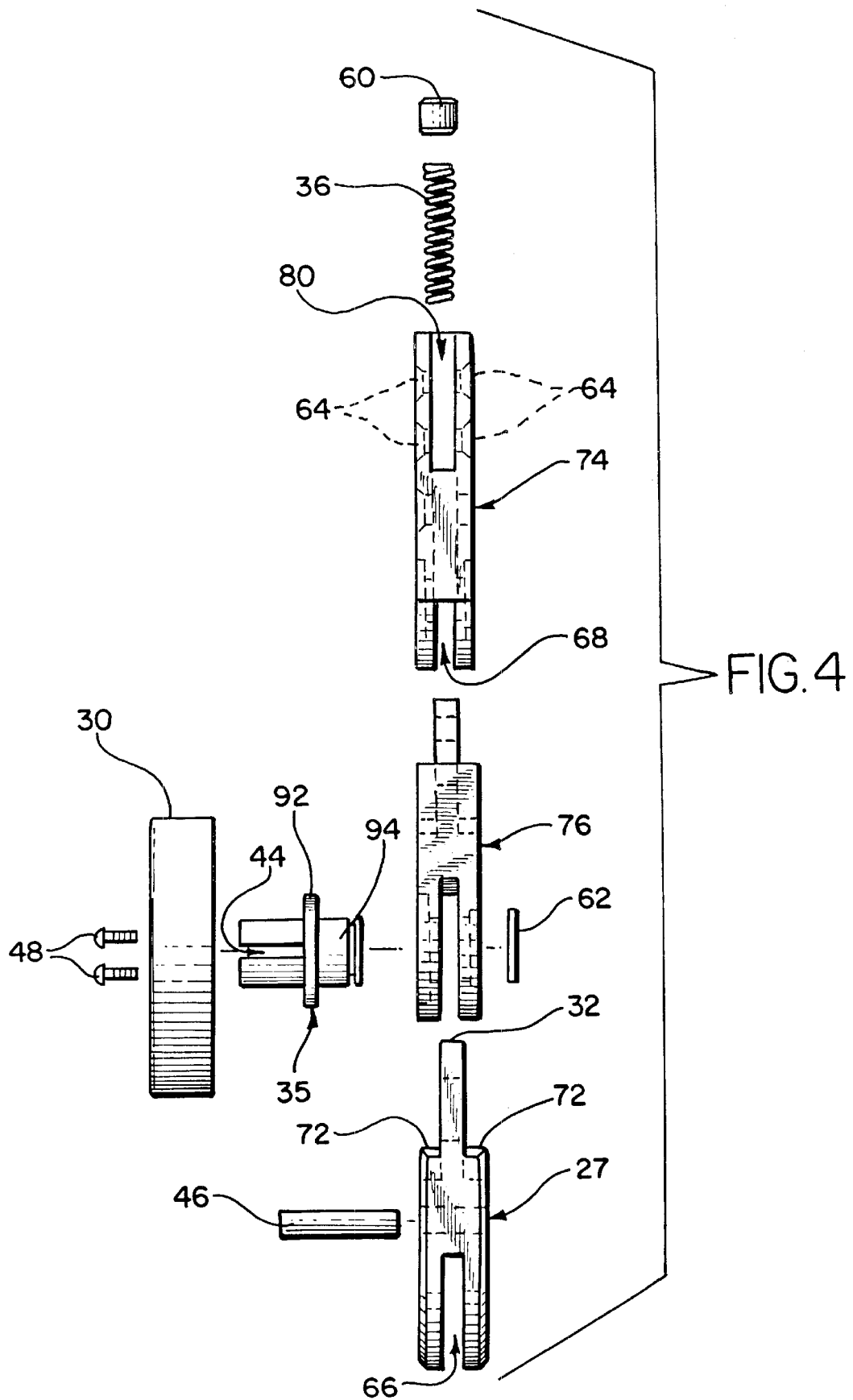

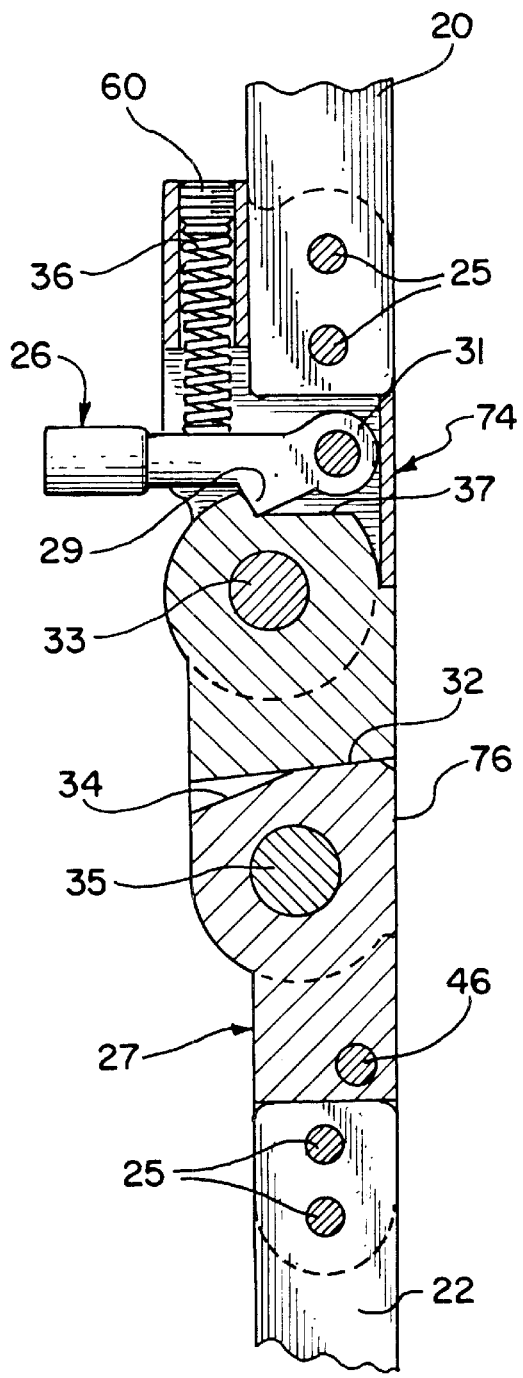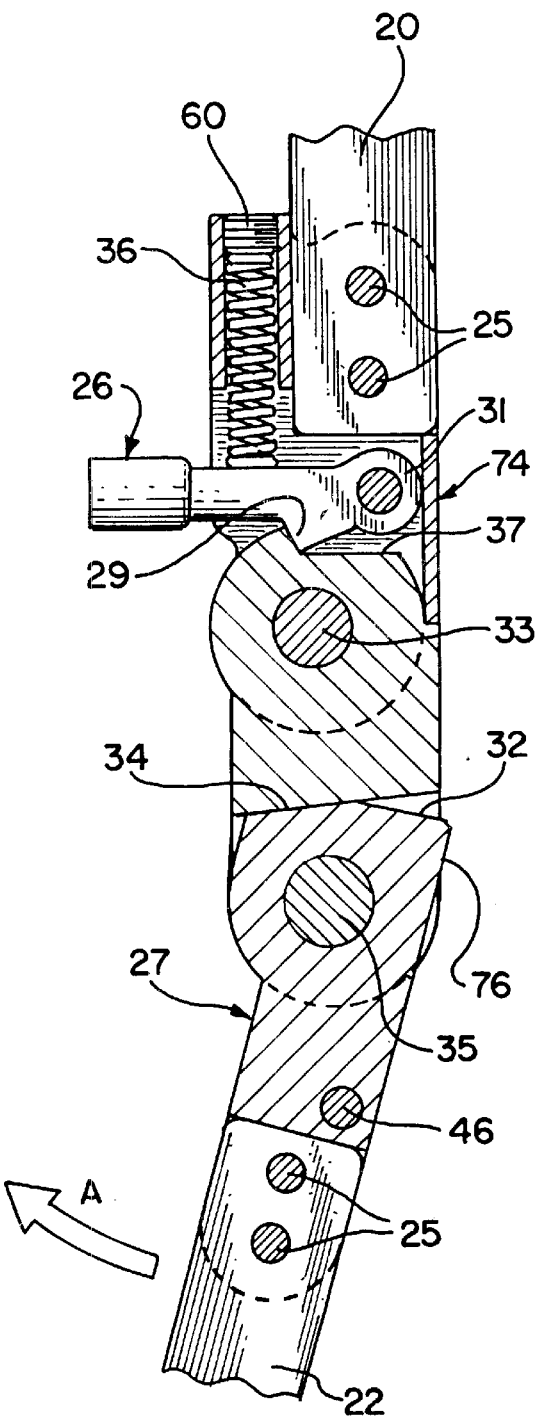

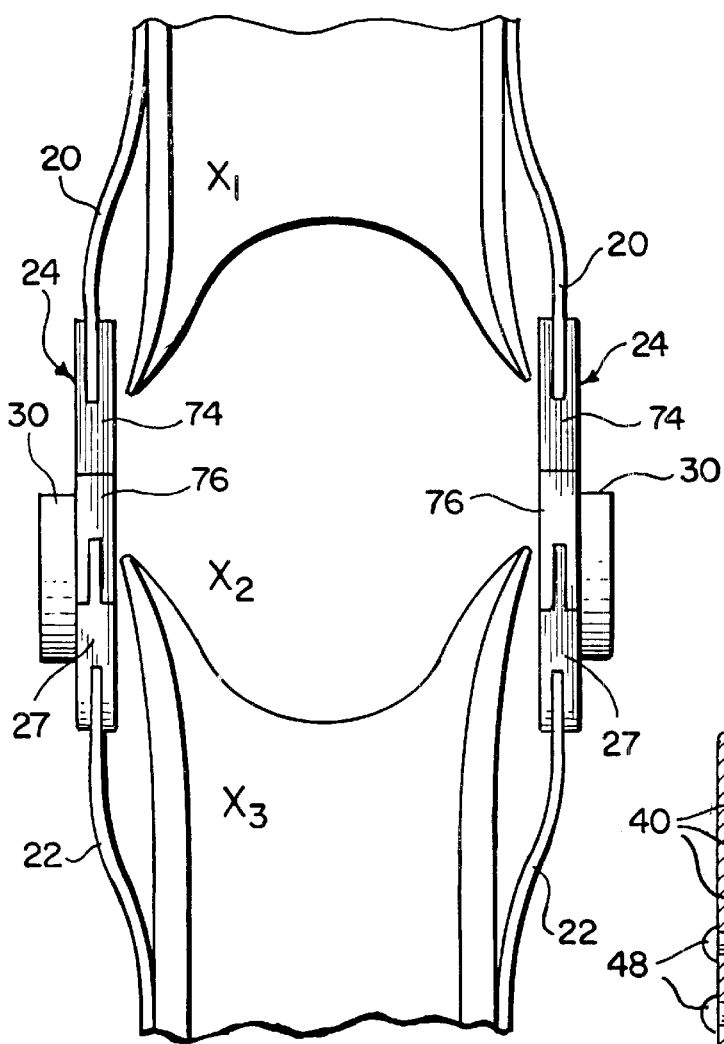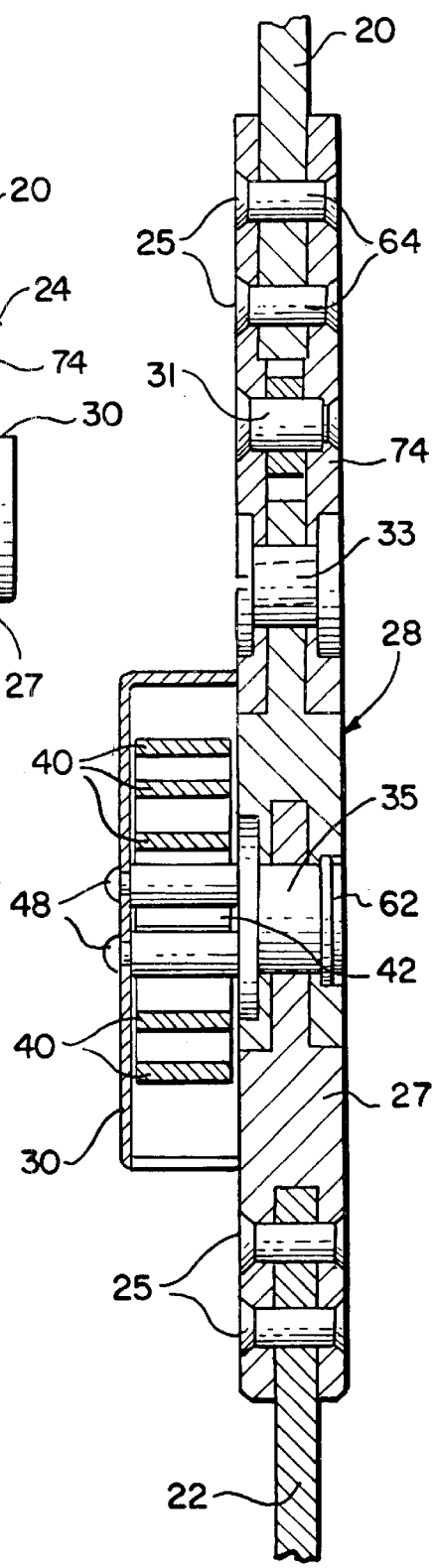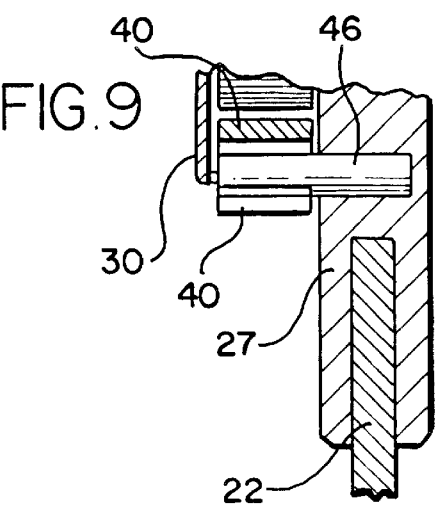

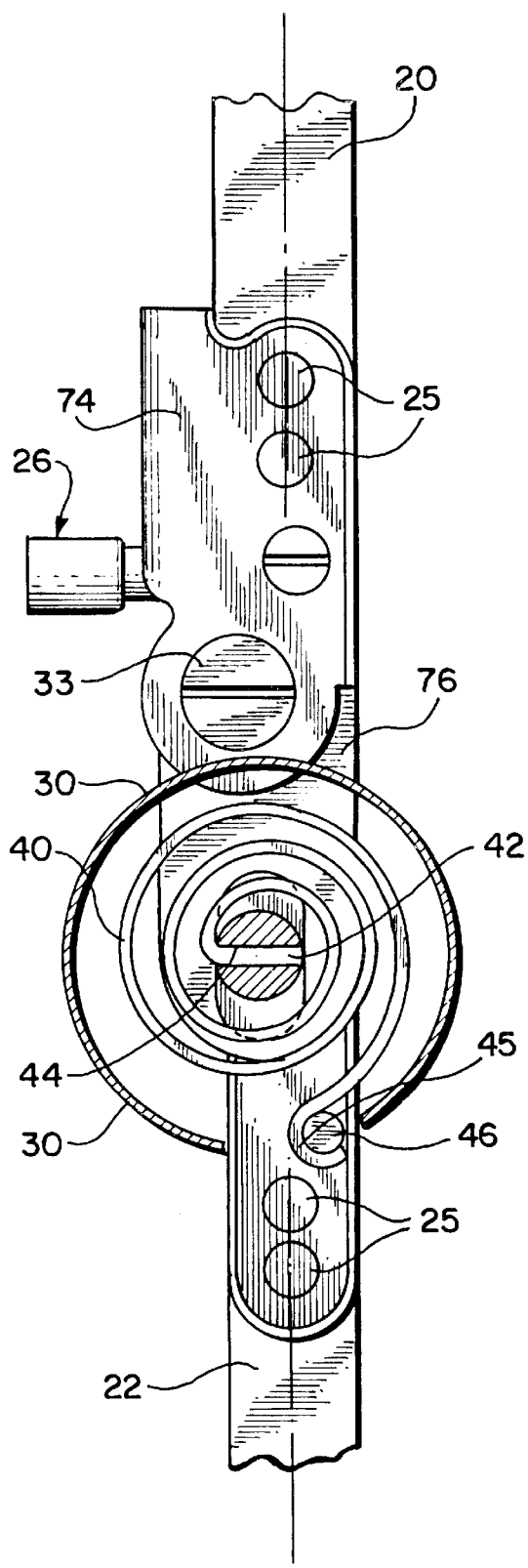
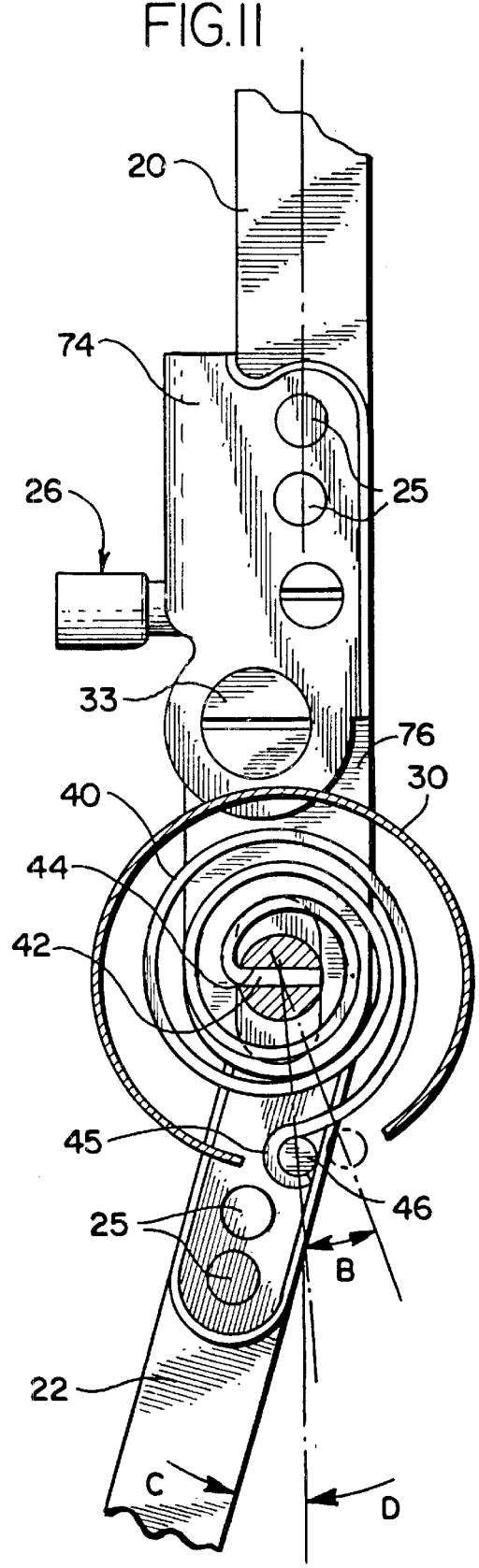

KNEE JOINT AND METHOD

FIELD OF THE INVENTION

This invention relates to a mechanical knee joint and method. More particularly, the invention relates to a knee orthosis or knee-ankle-foot orthosis and a mechanical knee joint incorporating a spring to control knee flexion and a method of providing desired resistance during knee flexion by use of the joint.

BACKGROUND OF THE INVENTION

Orthotic knee devices traditionally are utilized to aid and support guiding and limiting the range of motion of the human knee joint. A mechanical knee joint is frequently used to pivotally connect portions of the orthotic device secured to the body above and below the knee joint. Such a mechanical joint permits relative movement of the members and the associated body limbs and joints, to which the members are attached and the body joint to which the body parts are connected.

Typically a normal, healthy person flexes his or her knee through a range of about 18° from full extension during the loading response aspect of a normal gait cycle. During the normal stride of a normal person, there is a certain amount of natural muscle resistance during knee flexion in the quadriceps and hip muscles, for example. A patient with weak quadriceps muscles caused by, for example, polio, may have difficulty walking because the patient's knee can buckle during walking. A need exists for a knee joint that simulates the resistance that an individual encounters during a normal walking stride. A need also exists for a knee joint that can provide different amounts of resistance depending upon the muscle strength of a particular patient. A need exists for a knee joint that is easily adjustable among several different degrees of resistance. A need also exists for a knee joint and knee orthosis that provides a relatively constant resistance throughout the flexion movement and can be preloaded to a set amount of resistance when the joint is in the full extension position. A further need exists for a knee joint that provides such resistance without requiring numerous precise parts that require close tolerances.

SUMMARY OF THE INVENTION

In accordance with the present invention, a mechanical knee joint connecting two members for limited relative pivotal motion or movement is provided that provides resistant knee flexion. The orthotic knee joint comprises two members that are typically elongated, a structure associated with each member for permitting pivotal movement of one member relative to the other between extension and flexion positions and a torsion spring operatively associated with the bar members to provide torsional resistance to restrain pivotal movement of the bar members between the extension and flexion positions.

In accordance with another aspect of the present invention, a mechanical orthotic knee joint for pivotally connecting two orthotic members around an axis of rotation is provided comprising an upper and lower member, a structure associated with and connecting the upper and lower members for permitting movement of those members between extension and flexion positions and a torsion spring that is operatively associated with the members and extends longitudinally along the joint and one of the members to provide resistance to restrain pivotal movement.

Another aspect of the invention provides an orthotic appliance comprising a foot support, a lower bar member, an upper bar member, an orthotic ankle joint for pivotally connecting the foot support to the lower bar member, a first knee joint for permitting pivotal movement of the lower bar member relative to the upper bar member, a second knee joint for locking and releasing the upper bar member relative to the lower bar member such as when the wearer is in a sitting position, and a torsion spring to provide resistance during movement of the bar members from an extension position to a flexion position during rotational movement of the first knee joint.

Yet another aspect of the present invention is a method of providing a desired amount of resistance during flexion of a mechanical orthotic knee joint that comprises the steps of inserting a torsion spring into an orthotic device comprising two bar members connected by a mechanical knee joint.

Yet a further aspect of the present invention is a method of providing a uniform degree of resistance for a person wearing a knee joint comprising providing a knee joint of the present invention, wearing the device in any operative position on at least one of a patient's knees and walking with the knee joint in the operative position so that a desired level of resistance is achieved.

In one embodiment of the present invention, a torsion spring is loaded during flexion of the bar members. The loading of the torsion spring in the full extension position, as well as the type and size of the spring, determine the resistance in the joint. The torsion spring may also be used to limit the pivotal movement of the device.

In accordance with another aspect of the invention, the desired resistance in knee flexion can be easily and quickly adjusted to provide a greater or lesser amount of resistance. Torsion springs with different characteristics such as having different dimensions or composed of different materials may be readily removed from or inserted into the joint. In one embodiment of the present invention, the preload of tension in the torsion spring in the device can be adjusted. The amount of preload helps determine the initial resistance of the torsion spring in the fully extended position and aids in simulating the resistance and support during the walking stride of a healthy individual.

In accordance with yet another aspect of the present invention, the resistance during flexion is relatively constant. In the preferred embodiment, a substantial resistance can be obtained readily by use of a spiral torsion spring. In addition, the device of the present invention may be constructed to allow for different maximum ranges of flexion for different walking strides.

In accordance with another aspect of the present invention, one end of the torsion spring is operatively attached directly or indirectly to the upper member. Another end of the torsion spring is operatively attached to the lower member. To cause the lower member to pivot about the joint, sufficient force must be supplied to overcome the resistance of the torsion spring to compression.

Another aspect of the present invention provides a mechanical knee joint that is relatively simple to assemble, reliable and economical. The present invention uses a small number of parts and these parts to provide the desired resistance do not need to be machined or fabricated to close tolerances to work effectively.

For purposes of the present invention, "torsion spring" means a spiral torsion spring or leaf spring, including but not limited to a rectangular plate spring, triangular plate spring, rectangular plate spring with end tapered, compound leaf and laminated springs, laminated triangular plate springs, laminated rectangular plate spring with leaf ends tapered, laminated trapezoidal plate springs with leaf ends tapered, semielliptic springs, elliptic springs and spiral coil torsion springs of rectangular cross section. The preferred embodiment of the present invention utilizes a spiral torsion spring.

BRIEF DESCRIPTION OF THE DRAWINGS

FIG. 1 is a side elevation view of the orthotic appliance of the present invention in the fall extension position.

FIG. 2 is a side elevation view of the orthotic appliance of the present invention in the flexion position.

FIG. 3 is an exploded side view of a portion of the orthotic appliance of the present invention.

FIG. 4 is an exploded front view of a portion of the orthotic appliance of the present invention.

FIG. 5 is a sectional view of a portion of the orthotic appliance of the present invention in the full extension position.

FIG. 6 is a sectional view of a portion of the orthotic appliance of the present invention in the full flexion position.

FIG. 7 is a front elevation view of a portion of the knee brace of the present invention.

FIG. 8 is a sectional view of a portion of the knee brace of the present invention along line 8—8 of FIG. 1.

FIG. 9 is a sectional view of a portion of the knee brace of the present invention.

FIG. 10 is a side elevation view of the torsion spring of the present invention in the full extension position.

FIG. 11 is a side elevation view of the torsion spring of the present invention in the flexion position.

DETAILED DESCRIPTION OF THE INVENTION

Figure 16:
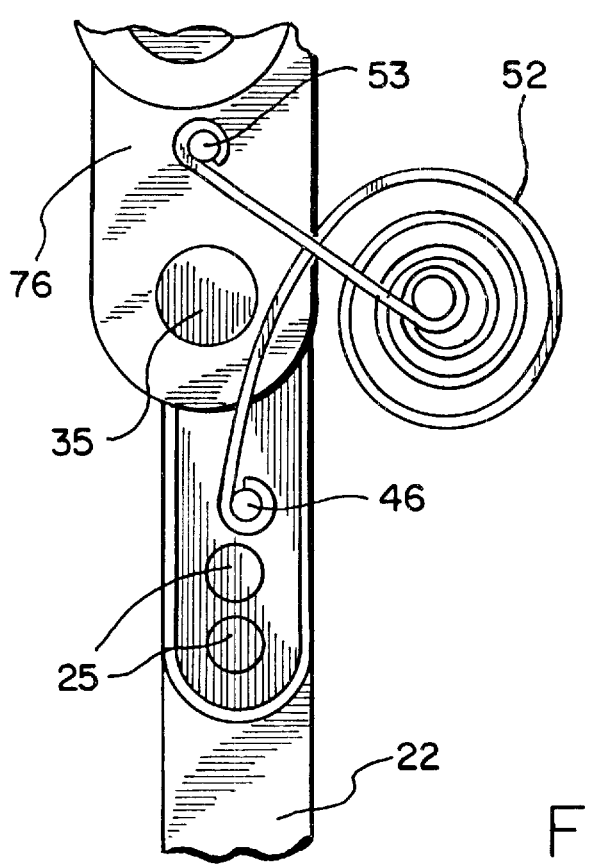
FIG. 16 is a side elevation view of an alternative embodiment of the knee joint of the present invention.

Referring to the figures generally and in particular to FIGS. 1–2, there is illustrated an orthotic device 10 on a person's leg L in accordance with the present invention. Orthotic device 10 is particularly useful for aiding a patient in walking. Orthotic device 10 includes two orthotic members joined together for permitting limited relative pivotal movement with respect to those members, in which the device provides resistance to pivotal movement during pivotal movement from an extended position to a flexed position. The device also provides a force tending to cause pivotal movement from a flexed position to an extended position. Although sometimes described in detail herein with respect to a knee orthosis, the mechanical orthotic device of the present invention is also applicable to an elbow orthosis.

Orthotic device 10 is composed of the plurality of cooperating components including foot support member 12, ankle joint 14, calf support member 15, upper support member 16, straps 18, upper bar member 20, lower bar member 22, first knee joint 24 and second knee joint 28. Foot support member 12, calf support member 15, upper support member 16, upper bar member 20, lower bar member 22, ankle joint 14, first knee joint 24 and second knee joint 28 may be contoured to portions of the anatomical shape of an individual patient's leg L.

Foot support member 12 is pivotally connected to lower bar member 22 by ankle joint 14. Ankle joint 14 utilizes a compression spring within plate 13 to allow a slight degree of restricted motion between foot support member 12 and lower bar member 22 under resistance. Lower bar member 22 is fastened to ankle joint 12 by any suitable structure such as by rivet 25.

Lower bar 22 and upper bar 20 are fastened to calf support 15 and upper support member 16 respectively. Straps 18 are placed at one or more locations partially around leg L. Straps 18 are attached to calf support 15 and upper support member 16 to help maintain appliance 10 in the proper place on a patient.

Turning now to FIGS. 3–11, first and second knee joints 24 and 28, respectively, are illustrated around upper leg $X_1$, knee $X_2$ and lower leg $X_3$. Lower elongated member 22 and upper elongated member 20 are pivotally connected at first knee joint 24 and second knee joint 28. It should be noted that clevis members 27, 74 and 76 may be fabricated as part of the lower end of upper member 20, and the upper end of lower member 22. As shown in FIGS. 3–6, first knee joint 24 comprises clevis member 74, latch 26, compression spring 36, channels 64, slots 68 and 80 and bushing 33. Upper bar member 20 slides in slot 80 of first knee joint 24 and is fixed within clevis member 74 by any suitable structure such as rivets 25 inserted into channels 64. Second knee joint 28 is secured within first knee joint 24 at slot 68 by bushing 35 as described below in further detail. As illustrated in FIG. 5, first knee joint 24 can be in a locked position. In the locked position, protrusion 29 of latch 26 lies flat against the indentation 37 of clevis member 74. In this position, upper bar member 20 can not move relative to the first knee joint 24. To move first knee joint 24 into the unlocked position, latch 26 is raised. By raising latch 26, rod 31 slides along clevis member 74 causing protrusion 29 to be raised from indentation 37. Such motion permits upper bar member 20 to be moved relative to first knee joint 24 over a range of just over 90 degrees. Typically, a patient lifts or activates latch 26 and moves the first knee joint 24 into the unlocked position when he or she is in a seated position to completely bend the knees. Spring 36, preferably a compression spring, provides resistance so that latch 26 is not activated accidentally and holds first knee joint 24 in the locked position. Spring 36 is held in place by lid 60.

Second knee joint 28, which is the primary knee joint of orthosis 10 is operatively associated with lower member 22 by any suitable structure such clevis member 27. Clevis member 27 comprises pin 46, channels 47, slot 66, aperture 90, ledges 72, first inclined shoulder portion 32 and second inclined shoulder portion 34. Lower bar member 22 fits into slot 66 of clevis member 27 and is secured by rivets 25 through channels 47. One end of clevis member 76 is inserted within clevis member 74 at slot 68. FIGS. 7–11 illustrate that second knee joint 28 is comprised of slotted bushing 35, torsion spring 40, cover 30, screws 48 and retaining clip 62 and the clevis members. It should be noted that these parts do not need to be highly machined or otherwise fabricated to close tolerances to achieve the desired degree of resistance and operation. Cover 30 protects spiral torsion spring 40 and is fixed to bushing 35 by screws 48 that fit in threaded apertures 99. Knee joint 28 pivots about slotted bushing 35 within a predetermined range. Bushing 35 defines the axis of rotation of the knee joint and has a slot 44, flange 92, threaded apertures 99 and bearing surface 94. Specifically, clevis member 27 preferably has a first inclined shoulder portion 32 and second inclined shoulder portion 34. In the full extended position of second knee joint 28, first inclined shoulder portion 32 lies flat relative to the bottom of second knee joint 28. First inclined shoulder portion 32 prevents any pivotal movement beyond this full extension position in any direction other than direction A. Second inclined shoulder portion 34 acts as a stop mechanism to prevent flexion beyond a certain point. As shown in FIG. 6, when lower bar member 22 pivots in direction A relative to upper bar member 20, second inclined shoulder portion 34 abuts against the bottom of second knee joint 28. At this point, no further relative pivotal movement is possible in direction A. Preferably, clevis member 27 is designed to permit relative pivotal movement throughout a range of 18 degrees, which is equal to the relative pivotal movement of a healthy knee joint during a normal walking stride. However, it is understood by those skilled in the art that any range of pivotal movement can be specified, such as a range of 15 or 25 degrees, by fashioning first inclined shoulder portion 32 and second inclined shoulder portion 34 appropriately. In addition, the torsion spring may be used to limit the pivotal movement of the joint beyond a certain point.

Turning now to FIGS. 10 and 11, there is illustrated a preferred spring in the present invention. Spiral torsion spring 40 is a torsion spring, and preferably a spiral coiled spring of rectangular cross section with approximately 3 coils and made of cold rolled and annealed carbon steel with a tension of 233 inch-pounds at 63 degrees of preload. The preferred spring has an active length of 11.5 inches, a width of 0.5 inches, an input thickness of 0.125 inches, a weight of 0.21 pounds, a density of 0.2840 pound per cubic inch and a stress of 178,944 psi. However, any suitable number of coils may be used and the torsion spring may be made of any suitable material, as long as it provides a desired tension. It is believed that use of a spiral spring allows the resistance to be relatively constant throughout a small range of compression. Torsion spring 40 may be located in any location in or around second knee joint 28 as long as one end of torsion spring 40 is connected directly or indirectly to lower bar member 22 and the other end of torsion spring 40 is connected directly or indirectly to upper bar member 20. Preferably, torsion spring 40 encompasses the axis of rotation of knee joint 28 or has a circumferential portion that extends around the axis of rotation of the joint.

Spring flat 42 is affixed within slot 44 of slotted bushing 35. Spring eye 45 wraps around pin 46. As lower bar member 22 flexes in direction D, pin 46 cooperates with spring eye 45 to load torsion spring 40, causing resistance to further movement. Alternatively, any structure for causing loading of torsion spring 40 during movement can be used. Because of first inclined shoulder portion 32 and second inclined shoulder portion 34, lower bar member 22 may only rotate through a range of motion B, which in the illustrated embodiment is about 18 degrees. When lower bar member 22 moves in direction C, torsion spring 40 unwinds urging joint 28 and orthotic device 10 into the full extension position. This design allows substantial resistance to be achieved readily. In the complete flexion position, the tension of torsion spring 40 is about 230 inch-pounds. Any suitable structure can be used to attach torsion spring 40 to bushing 35, which in the illustrated embodiment is slot 44 which retains spring flat 42 of torsion spring 40, for example.

Moreover, the resistance in the knee joint may be easily changed by substituting a spring of a different tension. Cover 30 is readily removed by unfastening screws 48 and torsion spring 40 can be removed from the knee joint. A different spring may be readily inserted to provide different resistance or a different amount of preload.

Figure 12:
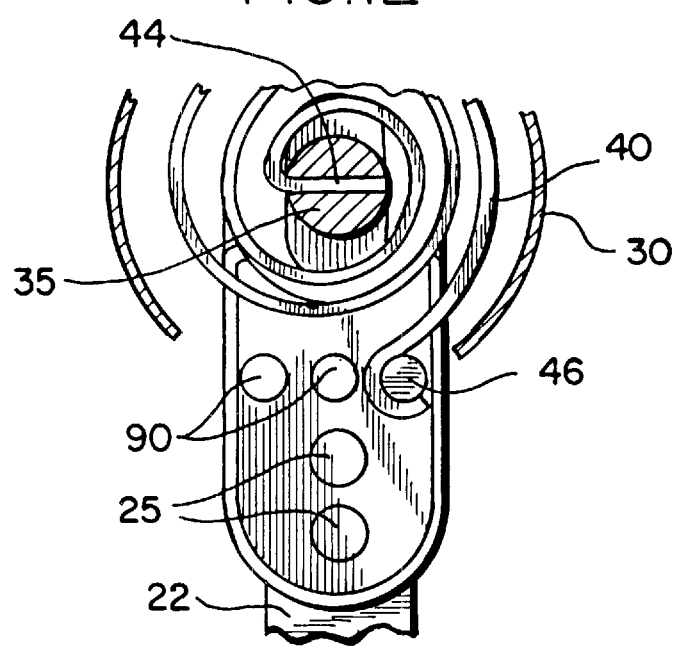
FIG. 12 is a side elevation view of an alternative embodiment of the knee joint of the present invention.

In an alternative embodiment, another way that the resistance in the orthotic device may be modified is by adjusting the location of pin 46 relative to torsion spring 40. As illustrated in FIG. 12, pin 46 may be placed within any of slots 90 permitting pin 46 to be moved relative to the center of torsion spring 40. The smaller the angle between the at rest position of the spring eye (relative to the center of the spring) and the position of pin 46 (relative to the center of the spring), the smaller the tension. Moving the pin permits fine tuning of the tension of the torsion spring. For larger scale adjustments to the resistance of the device, substituting springs may be more feasible.

Torsion spring 40 is preferably preloaded with a desired amount of tension. Preload refers to the amount of resistance in the knee joint in the fully extended position. In the fully extended position, torsion spring 40 is slightly compressed by pin 46 so that the desired torques are created and there is an initial resistance to pivotal movement. The amount of preload is determined by the desired range of motion of the knee joint and is often in the range of about between 40 and 55 degrees and preferably 49 degrees. At a preload of 49 degrees, the initial tension on the preferred spiral spring is between about 230 inch-pounds and 250 inch-pounds.

Figure 17:
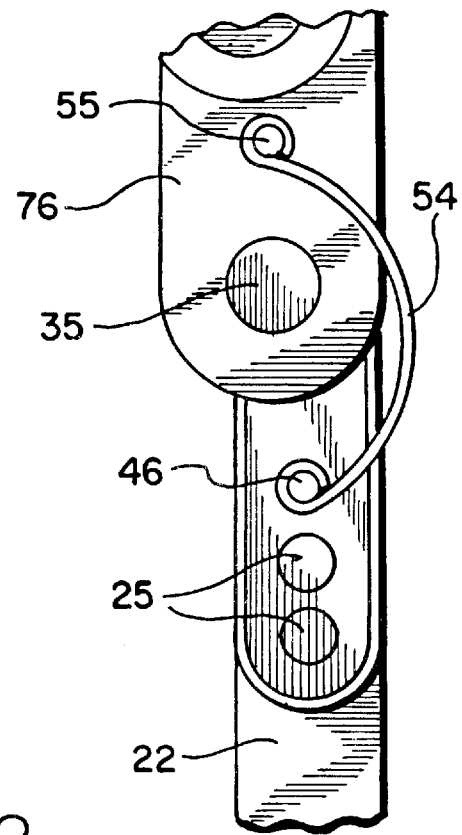
FIG. 17 is a side elevation view of an alternative embodiment of the knee joint of the present invention.
Figure 13:
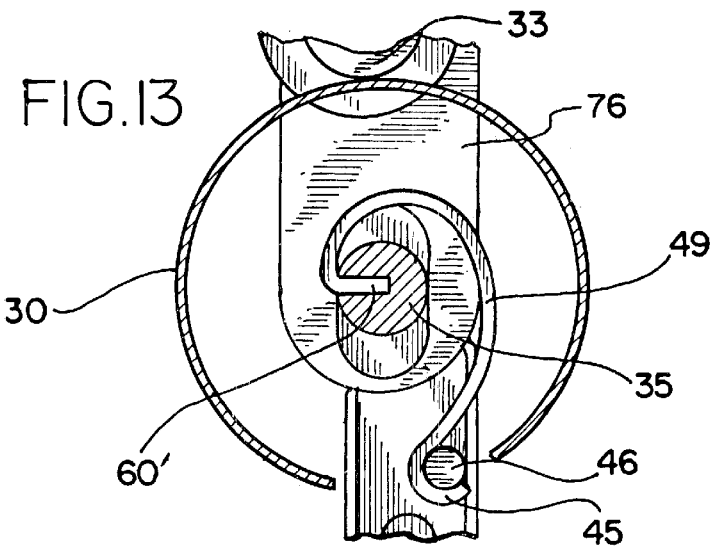
FIG. 13 is a side elevation view of an alternative embodiment of the knee joint of the present invention.
Figure 14:
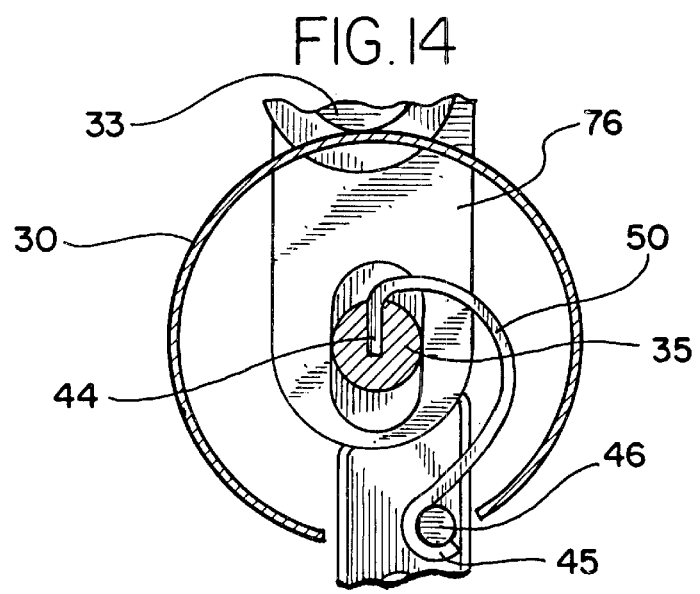
FIG. 14 is a side elevation view of an alternative embodiment of the knee brace of the present invention.
Figure 15:
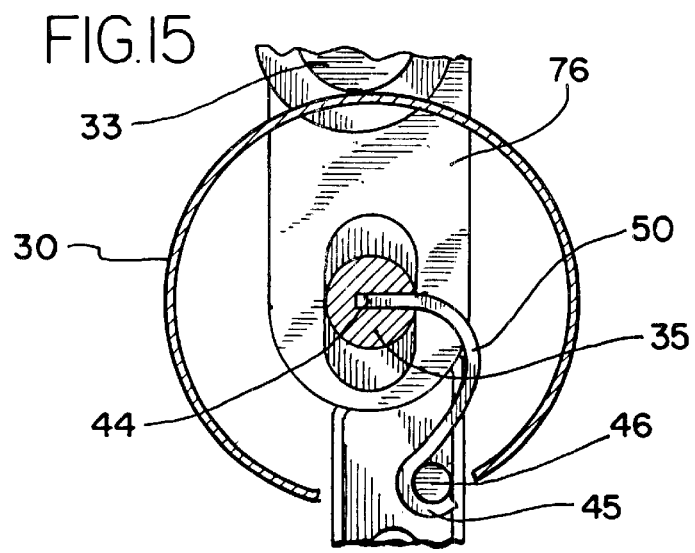
FIG. 15 is a side elevation view of an alternative embodiment of the knee brace of the present invention.

In FIGS. 13–17, there are illustrated alternative embodiments of the present invention. As shown in FIG. 13, spring 49 is attached to bushing 35 by partial slot 60'. Partial slot 60' can be any length or shape to sufficiently retain spring 49. FIGS. 14 and 15 shows the use of a spiral spring 50 with less than one coil. Spiral spring 50 encompasses the axis of rotation of the knee joint. Slot 44 in bushing 35 may be oriented in any direction as long as it sufficiently retains spring 50. FIG. 16 depicts the use of spiral spring 52 in the present invention. Spiral spring 52 is held in place by pins 46 and 53 and extends longitudinally along one of the bar members and does not encompass the axis of rotation of the knee joint. FIG. 17 depicts the use of a leaf spring 54. Leaf spring 54 extends longitudinally along one of the elongated member 22 and clevis member 76 (or portions thereof) and does not completely encompass the axis of rotation of the knee joint. The ends of leaf spring 54 are held in place by pins 46 and 55.

While the invention has been described with respect to certain preferred embodiments, as will be appreciated by those skilled in the art, it is understood that the invention is capable of numerous changes, modifications and rearrangements, and such changes, modifications and rearrangements are intended to be covered by the following claims.

We claim:

1. An orthotic joint for pivotally connecting two orthotic bar members around an axis of rotation comprising:
   a. an upper member;
   b. a lower member;
   c. means associated with and connecting the upper and lower members for permitting pivotal movement of the upper member relative to the lower member between extension and flexion positions; and
   d. a torsion spring to restrain pivotal movement of the upper and lower members between an extension and a flexion position, wherein only ends of the spring are secured, one end of the spring is operatively connected to the upper member and the other end of the spring is operatively connected to the lower member.

2. The orthotic joint of claim 1 wherein the spring is a spiral spring.

3. The orthotic joint of claim 2 wherein the spring has a circumferential portion that extends around the axis of rotation of the joint.

4. The orthotic joint of claim 2 wherein the spring encompasses the axis of rotation of the joint.

5. The orthotic joint of claim 2 wherein the spiral spring comprises a spring eye and a spring flat, the spring flat connected to the upper member and the spring eye connected to the lower member.

6. The orthotic joint of claim 5 wherein the spring eye is connected to the lower member by a pin.

7. The orthotic joint of claim 2 wherein the spring is preloaded with a desired amount of tension.

8. The orthotic joint of claim 2 wherein the spring is preloaded with between about 230 and 250 inch-pounds.

9. The orthotic joint of claim 8 wherein the leaf spring encompasses the axis of rotation of the joint.

10. The orthotic joint of claim 2 wherein the spring provides a force to facilitate pivotal movement of the upper and lower members between an extension and flexion portion.

11. The orthotic joint of claim 2 wherein the spiral spring has less than one coil.

12. The orthotic joint of claim 2 wherein the spiral spring has a rectangular cross section.

13. The orthotic joint of claim 1 further comprising a stop means preventing relative movement between the members beyond a predetermined amount.

14. The orthotic joint of claim 13 wherein the stop means prevents relative movement between the upper and lower members beyond 18 degrees.

15. The orthotic joint of claim 1 wherein the torsion spring is a leaf spring.

16. The orthotic joint of claim 1 wherein the joint is an elbow joint.

17. A mechanical orthotic knee joint for pivotally connecting two orthotic members around an axis of rotation comprising:
   a. an upper member;
   b. a lower member;
   c. means associated with and connecting the upper and the lower members for permitting movement of the upper member relative to the lower member between extension and flexion positions; and
   d. a spring to provide resistance to restrain pivotal movement of the upper and lower members between an extension to a flexion position, wherein only ends of the spring are secured, one end of the spring is operatively connected to the upper member and the other end of the spring is operatively connected to the lower member and wherein the spring extends longitudinally from the joint to at least one of the members.

18. An orthotic appliance comprising
   a. foot support;
   b. a lower bar member to support a leg below the knee;
   c. an upper bar member to support a leg above the knee;
   d. an orthotic ankle joint for pivotally connecting the foot support to the lower bar member;
   e. a first knee joint for permitting movement of the lower bar member relative to the upper bar member;
   f. a second knee joint for locking and releasing the upper bar member relative to the lower bar member wherein when the second knee joint is released, the upper bar member is at an approximately ninety degree angle with respect to the lower bar member; and
   g. a torsion spring, wherein the spring provides resistance during movement of the bar members from an extended to a flexed position and wherein the spring is attached to at least one of the bar members.

19. The orthotic appliance of claim 18 wherein the spring is a spiral spring.

20. The orthotic appliance of claim 19 wherein the spiral spring has a rectangular cross section.

21. The orthotic appliance of claim 19 wherein the spring has a circumferential portion that extends around the axis of rotation of the joint.

22. The orthotic appliance of claim 19 wherein the spiral spring comprises a spring eye and a spring flat, the spring flat connected to the upper member and the spring eye connected to the lower member.

23. The orthotic appliance of claim 22 wherein the spring eye is connected to the lower member by a pin.

24. The orthotic appliance of claim 19 wherein the spring is preloaded with a desired amount of tension.

25. The orthotic appliance of claim 19 wherein the spring is preloaded with between about 230 and 250 inch-pounds.

26. The orthotic appliance of claim 19 wherein the spring provides a force to facilitate pivotal movement to the upper and lower members between an extension and flexion portion.

27. The orthotic appliance of claim 19 wherein the spiral spring has less than one coil.

28. The orthotic appliance of claim 18 wherein said first knee joint has a stop means preventing relative movement between the members beyond a predetermined amount when the second knee joint is locked.

29. The orthotic appliance of claim 28 wherein the stop means prevents relative movement between the upper and lower members beyond 18 degrees.

30. The orthotic appliance of claim 18 wherein the torsion spring is a leaf spring.

31. The orthotic appliance of claim 30 wherein the leaf spring encompasses the axis of rotation of the joint.

32. A method for providing a desired amount of resistance during flexion of a mechanical orthotic knee joint comprising:
   a. providing an orthotic device comprising an upper and lower member and a means associated with and connecting the upper and lower members for permitting pivotal movement of the upper member relative to the lower member between extension and flexion positions; and
   b. providing the device with a torsion spring having a desired level of tension wherein only ends of the spring are secured, one end of the spring is operatively connected to the upper member and the other end of the spring is operatively connected to the lower member.

33. The method recited in claim 32 comprising the further step of engaging the knee joint in the operative position so that the desired amount of resistance is provided during flexion.

34. A method of providing a uniform degree of resistance for a person using a knee joint during walking comprising:
   a. providing an orthotic device comprising an upper and lower member, a means associated with and connecting the upper and lower members for permitting pivotal movement of the upper member relative to the lower member between extension and flexion positions and a torsion spring to provide uniform resistance during pivotal movement between an extension and flexion position wherein only ends of the spring are secured, one end of the spring is operatively connected to the upper member and the other end of the spring is operatively connected to the lower member;

b. wearing the device in operative position as a knee joint for at least one of the person's knees; and c. walking with the knee joint in the operative position on a person's limb so that a desired degree of uniform resistance is provided during flexion.

\* \* \* \* \*

UNITED STATES PATENT AND TRADEMARK OFFICE
CERTIFICATE OF CORRECTION

PATENT NO.      : 6,471,664 B1
DATED           : October 19, 2002
INVENTOR(S)     : James H. Campbell et al.

It is certified that error appears in the above-identified patent and that said Letters Patent is hereby corrected as shown below:

Column 7,
Line 58, after "a." insert -- a --.

Signed and Sealed this

Sixth Day of May, 2003

JAMES E. ROGAN
*Director of the United States Patent and Trademark Office*